(12) United States Patent
Campbell et al.

(10) Patent No.: US 6,300,335 B1
(45) Date of Patent: *Oct. 9, 2001

(54) 4-AMINOQUINAZOLINE DERIVATIVE CGMP-PDE INHIBITORS FOR THE TREATMENT OF ERECTILE DYSFUNCTION

(75) Inventors: Simon Fraser Campbell; Alexander Roderick Mackenzie; Anthony Wood, all of Sandwich (GB)

(73) Assignee: Pfizer Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/836,670
(22) PCT Filed: Oct. 16, 1995
(86) PCT No.: PCT/EP95/04066
  § 371 Date: May 22, 1997
  § 102(e) Date: May 22, 1997
(87) PCT Pub. No.: WO96/16644
  PCT Pub. Date: Jun. 6, 1996

(30) Foreign Application Priority Data

Nov. 26, 1994 (GB) .................................................. 9423910

(51) Int. Cl.$^7$ ................................................ A61K 31/504
(52) U.S. Cl. ............................................................ 514/260
(58) Field of Search ............................................ 514/260

(56) References Cited

U.S. PATENT DOCUMENTS

| | | |
|---|---|---|
| 4,521,421 | 6/1985 | Foreman . |
| 5,436,233 * | 7/1995 | Lee et al. ............................. 514/63 |

FOREIGN PATENT DOCUMENTS

| | | | |
|---|---|---|---|
| 0293063 | 11/1988 | (EP) . | |
| 0371731 | 6/1990 | (EP) . | |
| 0442204 | 8/1991 | (EP) . | |
| 0463756 | 1/1992 | (EP) . | |
| 0526004 | 3/1993 | (EP) . | |
| 0535924 | 4/1993 | (EP) . | |
| 2547501 | 12/1984 | (FR) ............................. | A61K/17/00 |
| 03044324 | 2/1991 | (JP) ............................. | A61K/31/52 |
| 8910123 | 11/1989 | (WO) ............................ | A61K/31/35 |
| 9306104 | 4/1993 | (WO) . | |
| 9307149 | 4/1993 | (WO) . | |
| 9312095 | 6/1993 | (WO) . | |
| 9400453 | 1/1994 | (WO) . | |
| 9405661 | 3/1994 | (WO) . | |
| 9428902 | 12/1994 | (WO) ........................ | A61K/31/505 |
| 9429277 | 12/1994 | (WO) ........................ | C07D/233/38 |

OTHER PUBLICATIONS

Excerpts from the UCLA doctoral dissertation of Margaret Ann Bush, including pp. ii–xvii, 1 and 154–161, 1995.

Karl–Erik Anderson et al. The American Physiological Society, 1995, vol. 75, pp. 191–236.
W. Meinhardt et al., International Journal of Impotence Research, 1997, vol. 9, pp. 17–26.
F. Holmquist et al., Arta Physil Scand, 1991, vol. 143, pp. 299–304.
M. F. Meyer et al., Ann Urol., 1993, vol. 27, No. 3, pp. 179–182.
Y.–M. Lin et al., Urol. Res, 1990, vol. 24., pp. 27–32.
Harvey C. Taub, et al., Urology, 1993, vol. 42, No. 6, pp. 698–704.
Am. J. Physiol. Heart Circ. Physiol., vol. 264, No. 2, 1993, p 419–422.
Neurol Urodyn, vol. 13, No. 1, 1994, p 71–80.
J. Urol., Trigo–Rocha, V. 149, 872–877, 1993.
ABPI Data Sheet Compendium, 1990–1991; pp. 740–742.
Rote Liste 1992, (along with English translation), Entries 36073–077, 54108–110, 1992.
Medicinal and Poisonous Plants in Southwest Africa, Ebrhard von Koenen, 1979 (along with English translation).
Pharmacological Expert Opinion on the Use of cGMP Inhibitors for the Oral Treatment of Erectile Dysfunction in Men, Professor J. C. Frolich, Exhibit 2, (along with english translation), Dec. 10, 1998.
Journal of Japanese Society of Urology, Oct. 1992, vol. 83, No. 1, pp. 1655–1661, Yasuo Kawanishi, et al.
Optimizing Therapy with Methylxanthines, Ekkehard Haen, et al. Aug. 1989 (along with English translation); C1435–C1440.
Hagers Handbuch Der Pharmazeutischen Praxis, begonnen Von W. Kern, et al., 1971, p. 675–676 (along with English translation).
Br. J. Phamacol. 1992, 106, 1028–1034, Jacob de Boer, et al.
The Journal of Urology, vol. 149, Apr. 1993, No. 4, AUA Eighty–Eighth Annual Meeting May 15–20, Abstract 285.
Physician's Desk Reference, 1992, 46th Edition, pp. 1099–1100.
Trends in Pharmacological Sciences, Jan. 1991, vol. 12, No. 1, C. David Nicholson, et al., pp. 150–155.
CNN—Viagra? No, Vuka, Vuka, Jun. 19, 1998.
Pharmac. Ther. vol. 51, pp. 13–33, 1991, W. Joseph Thompson.
Aronson et al., J. Urol. 147 Supp 454A, 1992, No. 967.
International Journal of Impotence Research, vol. 6, No. 1, Mar. 1994, A. W. Zorgniotti, et al, pp. 33–36.
Postgraduate Medicine, Treatment alternatives for impotence, E. Douglas Whitehead, et al, pp. 139–145, Aug. 2, 1990.

(List continued on next page.)

*Primary Examiner*—Rebecca Cook
(74) *Attorney, Agent, or Firm*—Peter C. Richardson; Gregg C. Benson; James T. Jones

(57) ABSTRACT

4-aminoquinazoline derivatives which are selective inhibitors of cGMP PDE are useful in the treatment of erectile dysfunction (impotence) in male animals, including man.

3 Claims, No Drawings

OTHER PUBLICATIONS

Drug Therapy, Aug. 1989, Treating Erectile Dysfunction, I.J. Fishman, pp. 102–111.

Molecular Pharmacology, vol. 36, No. 5, Nov. 1989, Peter G. Gillespie, and Joseph A. Beavo, pp. 773–781.

J. Mol. Cell Cardiol, 1980, 12/10 (939–954), Abstract.

Postgraduate Medicine, vol. 93, No. 3, Management of Impotence, John E. Morley, pp. 65–72, Feb. 15, 1993.

Biochemical Pharmacology, vol. 46, No. 5, pp. 833–839, 1993, T. Saeki et al.

Tohoku J. Exp. Med., 1991, 165, Yoshlastu Takahashi, et al, pp. 49–58.

Br. J. Dis. Chest, 1986, 80, J. Reiser, et al, pp. 157–163.

Journal of Medicine, vol. 10, No. 6, 1979, J. L. Ambrus, et al, pp. 445–456.

Br. J. Pharmacol., 1993, 108, 562–568, J. Cortijo, et al.

Journal of Ethnopharmacology, 12, 1984, 36–74, Hans–Joechim Arnold, et al.

Journal of Pharm. & Exper. Therapeutics, 1989, E. G. McMahon, et al, pp. 1000–1005.

British Journal of Diseases of the Chest, Robin M. Rudd, et al, 1988, 77, pp. 78–86.

The Journal of Urology, vol. 145, No. 4, 1991, AUA Eighty–sixth Annual Meeting Jun. 2–6, 1991, p. 341A, Abstract 516.

Martindale The Extra Pharmacopoeia, 29th Ed., 1989, p. 1423, heading 14026–m.

Archives of Pharmacology, W. R. Kukovetz, Evidence for Cyclic GMP–Mediated Relaxant Effects of Nitro–Compounds in Coronary Smooth Muscle, 1979.

Journal of the American Geriatrics Society, vol. 41, No. 4, 1993, Stanley G. Korenman, et al., p. 363–366.

Angiology—Journal of Vascular Diseases, 1991, pp. 418–420 Kent S. Allenby, et al.

Clin. Res., vol. 36(1), 123(A), Korenmann SG, Treatment of Vasculogema Sexual Dysfunction with pentoxyfylline, 1988.

American Physiological Society, Joseph A. Beavo, Cyclic Nucleotide Phosphodiesterases: Functional Implications of Multiple Isoforms, pp. 725–748, 1995.

Pharmacological Activities of the Main Metabolite of Flavoxate 3–Methylflavone–8–carboxylic Acid, Arzenmittel–Forschung, P. Cazzulani, et al, pp. 379–382, 1988.

Trends in Pharmacological Sciences, vol. 11, No. 4, 1990, Joseph A. Beavo, et al. pp. 19–27.

ABPI compendium—Trental 400 summary sheet, 1990.

Taher et al, Int. J. Impotence Res., 1992 vol. 4, Suppl. 2, p. 11.

Bowman et al, Br. J. Pharmacol., 81, 665–674, 1984.

Murray, DN&P, 6, 1993, 150–156.

Rajfer et al., NEJ Med., 326, 90–94, 1992.

Bush et al, J. Urol., 147, 1650–1655, 1992.

Am. J. Pysiol., V. 264, No. 2, pp. 419–422, 1993.

Abstracts of Papers American Chemical Society, vol. 210, No. 1–2, 1995, Abstr. 229.

* cited by examiner

4-AMINOQUINAZOLINE DERIVATIVE CGMP-PDE INHIBITORS FOR THE TREATMENT OF ERECTILE DYSFUNCTION

This is a National Phase filing under 35 USC §371 based on PCT/EP95/04066 which was filed internationally on Oct. 16, 1995 and which was published internationally as WO 96/16644 on Jun. 6 ,1996.

This invention relates to the use of compounds which are selective inhibitors of cyclic guanosine 3',5'-monophosphate phosphodiesterases (cGMP PDEs) in the treatment of erectile dysfunction (impotence) in male animals, including man.

Impotence can be defined literally as a lack of power, in the male, to copulate and may involve an inability to achieve penile erection or ejaculation, or both. More specifically, erectile impotence or dysfunction may be defined as an inability to obtain or sustain an erection adequate for intercourse. Its prevalence is claimed to be between 2 and 7% of the human male population, increasing with age, up to 50 years, and between 18 and 75% between 55 and 80 years of age. In the USA alone, for example, it has been estimated that there are up to 10 million impotent males, with the majority suffering from problems of organic rather than of psychogenic origin.

Reports of well-controlled clinical trials in man are few and the efficacy of orally administered drugs is low. Although many different drugs have been shown to induce penile erection, they are only effective after direct injection into the penis, e.g. intraurethrally or intracavernosally (i.c.), and are not approved for erectile dysfunction. Current medical treatment is based on the i.c. injection of vasoactive substances and good results have been claimed with phenoxybenzamine, phentolamine, papaverine and prostaglandin $E_1$, either alone or in combination; however, pain, priapism and fibrosis of the penis are associated with the i.c. administration of some of these agents. Potassium channel openers (KCO) and vasoactive intestinal polypeptide (VIP) have also been shown to be active i.c., but cost and stability issues could limit development of the latter. An alternative to the i.c. route is the use of glyceryl trinitrate (GTN) patches applied to the penis, which has been shown to be effective but produces side-effects in both patient and partner.

As a general alternative to pharmacological intervention, a variety of penile prostheses has been used to assist achievement of an erection. The short term success rate is good, but problems with infection and ischaemia, especially in diabetic men, make this type of treatment a final option rather than first-line therapy.

According to the specification of our International patent application no PCT/EP94/01580, (publication no WO94/28902), we describe and claim the use of a series of pyrazolo [4,3-d]pyrimidin-7-ones for the treatment of impotence. The compounds are potent and selective inhibitors of cGMP PDE in contrast to their inhibition of cyclic adenosine 3',5'-monophosphate phosphodiesterases (cAMP PDEs). This selective enzyme inhibition leads to elevated cGMP levels which, in turn, provides the basis for the utilities previously disclosed for the compounds in the treatment of stable, unstable and variant (Prinzmetal) angina, hypertension, pulmonary hypertension, congestive heart failure, atherosclerosis, conditions of reduced blood vessel patency, peripheral vascular disease, stroke, bronchitis, allergic asthma, chronic asthma, allergic rhinitis, glaucoma, and diseases characterised by disorders of gut motility, e.g. irritable bowel syndrome. The specification goes on to describe investigations which identified three PDE isoenzymes in human corpus cavenosum tissue, relaxation of which leads to penile erection. The predominant enzyme was found to be the cGMP-specific $PDE_V$, while cGMP-stimulated cAMP $PDE_{II}$ and cGMP-inhibited cAMP $PDE_{III}$, were also present. The compounds described were found to be potent and selective inhibitors of the $PDE_V$ enzyme but demonstrated only weak inhibitory activity against the $PDE_{II}$ and $PDE_{III}$ enzymes. This activity is believed to be responsible for the action of the compounds in the treatment of erectile dysfunction.

A number of cGMP-PDE inhibitors have previously been described in the literature for a variety of utilities, these include use in treating obstructive lung diseases such as asthma and brochitis, in combatting allergic diseases such as allergic asthma, allergic rhinitis, urticaria, and irritable bowel syndrome; and in combatting angina, hypertension and congestive heart failure. Utility has also been claimed as diuretics, as antiinflammatory agents, in the treatment of baldness, for conditions of reduced blood vessel patency, and in glaucoma. However there has not previously been any suggestion that any of these compounds would be of utility in the treatment of erectile dysfunction.

Thus the present invention provides the use of a compound which is a selective cGMP PDE inhibitor for the manufacture of a medicament for the treatment of erectile dysfunction in a male animal, including man, wherein said compound is:

i a 5-substituted pyrazolo [4,3-d]pyrimidine-7-one as disclosed in European patent application 0201188;
ii a griseolic acid derivative as disclosed in European patent applications nos 0214708 and 0319050;
iii a 2-phenylpurinone derivative as disclosed in European patent application 0293063;
iv a phenylpyridone derivative as disclosed in European patent application 0347027;
v a fused pyrimidine derivative as disclosed in European patent application 0347146;
vi a condensed pyrimidine derivative as disclosed in European patent application 0349239;
vii a pyrimidopyrimidine derivative as disclosed in European patent application 0351058;
viii a purine compound as disclosed in European patent application 0352960;
ix a quinazolinone derivative as disclosed in European patent application 0371731;
x a phenylpyrimidone derivative as disclosed in European patent application 0395328;
xi an imidazoquinoxalinone derivative or its aza analogue as disclosed in European patent application 0400583;
xii a phenylpyrimidone derivative as disclosed in European patent application 0400799;
xiii a phenylpyridone derivative as disclosed in European patent application 0428268;
xiv a pyrimidopyrimidine derivative as disclosed in European patent 0442204;
xv a 4-aminoquinazoline derivative as disclosed in European patent application 0579496;
xvi a 4,5-dihydro-4-oxo-pyrrolo[1,2-a]quinoxaline derivative or its aza analogue as disclosed in European patent application 0584487;
xvii a polycyclic guanine derivative as disclosed in International patent application WO91/19717;
xviii a nitrogenous heterocyclic compound as disclosed in International patent application WO93/07124;
xix a 2-benzyl-polycyclic guanine derivative as disclosed in International patent application WO 94/19351;
xx a quinazoline derivative as disclosed in U.S. Pat. No. 4060615;

xxi a 6-heterocyclyl pyrazolo [3,4-d]pyrimidin-4-one as disclosed in U.S. Pat. No. 5,294,612;

xxii a benzimidazole as disclosed in Japanese patent application 5-222000; or xxiii a cycloheptimidazole as disclosed in European Journal of Pharmacology, 251, (1994), 1.

xxiv a N-containing heterocycle as disclosed in International patent application WO94/22855.

The invention includes the use of any compound within the scope of the claims of the patents listed above as well as the particular individual compounds disclosed therein.

Of particular interest for use in the present invention are compounds disclosed in EP 0579496, WO93/07124, U.S. Pat. No. 5,294,612 and WO94/22855 (xv, xviii, xxi and xxiv above); the compounds of EP 0579496 and WO94/22855 being especially preferred.

Examples of particular and preferred compounds from these patents and publications for use in the present invention include:

1,3-dimethyl-5-benzylpyrazolo[4,3-d]pyrimidine-7-one (preparation as described in European patent application 201188, Example 1), 2-(2-propoxyphenyl)-6-purinone (preparation as described in European patent application 0293063, Example 1), 6-(2-propoxyphenyl)-1,2-dihydro-2-oxopyridine-3-carboxamide (preparation as described in European patent application 0347027, Example 2), 2-(2-propoxyphenyl)pyrido[2,3-d]pyrimid-4(3H)-one (preparation as described in European patent application 0347146, Example 1), 7-methylthio-4-oxo-2-(2-propoxyphenyl)-3,4-dihydropyrimido[4,5-d]pyrimidine (preparation as described in European patent application 0351058, Example 1), 6-hydroxy-2-(2-propoxyphenyl)pyrimidine-4-carboxamide (preparation as described in European patent application 0395328, Example 15), 1-ethyl-3-methylimidazo[1,5a]quinoxalin-4(5H)-one (preparation as described in European patent application 0400583), 4-phenylmethylamino-6-chloro-2-(1-imidazoloyl) quinazoline (preparation as described in European patent application 0579496, Example 5(c)), 5-ethyl-8-[3-(N-cyclohexyl-N-methylcarbamoyl)-propyloxy]-4,5-dihydro-4-oxo-pyrido[3,2-e]pyrrolo[1,2-a]pyrazine (preparation as described in European patent application 0584487, Example 1), 5'-methyl-3'-(phenylmethyl)-spiro[cyclopentane-1,7'(8'H)-(3'H)-imidazo[2,1-b]purin]4'(5'H)-one (preparation as described in International patent application WO 91/19717, Example 9A3), 1-[6-chloro-4-(3,4-methylenedioxybenzyl) aminoquinazolin-2-yl)piperidine-4-carboxylic acid (preparation as described in International patent application WO93/07124), (6aR,9aS)-2-(4-trifluoromethylphenyl)methyl-5-methyl-3,4,5,6a,7,8,9,9a-octahydrocyclopent[4,5]imidazo[2,1-b]purin-4-one(preparation as described in International Patent application WO94/19351, Example 14), 1-tert-butyl-3-phenylmethyl-6-(4-pyridyl)pyrazolo[3,4-d]pyrimid-4-one (preparation as described in U.S. Pat. No. 5,294,612, Example 90), 1-cyclopentyl-3-methyl-6-(4-pyridyl)-4,5-dihydro-1H-pyrazolo[3,4-d]pyrimid-4-one, (preparation as described in U.S. Pat. No. 5,294,612, Example 83), 2-butyl-1-(2-chlorobenzyl)6-ethoxycarbonylbenzimidazole (preparation described in Japanese patent application 5-222000), 2-(4-carboxypiperidino)-4-(3,4-methylenedioxybenzyl) amino-6-nitroquinazoline (preparation described in International patent application WO94/22855, Example II), and 2-phenyl-8-ethoxycycloheptimidazole (KT2-734).

Of particular interest for use in the present invention are the compounds: 4-phenylmethylamino-6-chloro-2-(1-imidazoloyl)quinazoline (preparation as described in European patent application 0579496, Example 5(c)), 1-[6-chloro-4-(3,4-methylenedioxybenzyl)aminoquinazolin-2-yl)piperidine-4-carboxylic acid (preparation as described in International patent application WO93107124), (6aR,9aS)-2-(4-trifluoromethylphenyl)methyl-5-methyl-3,4,5,6a,7,8,9,9a-octahydrocyclopent[4,5]imidazo[2,1-b]purin-4-one (preparation as described in International Patent application W094/19351, Example 14), 1-tert-butyl-3-phenylmethyl-6-(4-pyridyl)pyrazolo[3,4-d]pyrimid-4-one (preparation as described in U.S. Pat. No. 5,294,612, Example 90), 1-cyclopentyl-3-methyl-6-(4-pyridyl)-4,5-dihydro-1H-pyrazolo[3,4-d]pyrimid-4-one, as described in U.S. Pat. No. 5,294,612, Example 83), or 2-(4-carboxypiperidino)-4-(3,4-methylenedioxybenzyl)amino-6-nitroquinazoline (preparation described in International patent application WO94/22855, Example II), Further cGMP PDE inhibitors for use in the treatment of erectile dysfunction are:

xxv a pyrazolopyrimidine derivative as disclosed in European patent application 0636626;

xxvi a 4-aminopyrimidine derivative as disclosed in European patent application 0640599;

xxvii a imidazoquinazoline derivative as disclosed in International patent application WO95/06648;

xxviii an anthranilic acid derivative as disclosed in International patent application WO95/18097;

xxix a 4-aminoquinoline derivative as disclosed in U.S. Pat. No. 5,436,233;

xxx a tetracyclic derivative as disclosed in International patent application WO95/19978;

xxxi a imidazoquinazoline derivative as disclosed in European patent pplication 0668280; or xxii a quinazoline compound as disclosed in European patent application 669324. The compounds may be evaluated as selective inhibitors of cGMP-PDE using any of the methods previously described but in particular their activity against cGMP-PDE$_V$ may be assessed as described in our International patent application PCT/EP94/01580, (WO94/28902).

Generally, in man, oral administration is the preferred route, being the most convenient and avoiding the disadvantages associated with i.c. administration. A preferred dosing regimen for a typical man is 5 to 75 mg of compound daily, however the dosage may be increased depending on the potency of the compound being administered and higher dosages are within the scope of the invention. Alternative dosage regimes are also possible depending upon the individual patients circumstances such as the frequency of sexual intercourse. In circumstances where the recipient suffers from a swallowing disorder or from impairment of drug absorption after oral administration, the drug may be administered parenterally, e.g. sublingually or buccally.

For veterinary use, a compound of the invention or a non-toxic salt thereof is administered as a suitably acceptable formulation in accordance with normal veterinary practice and the veterinary surgeon will determine the dosing regimen and route of administration which will be most appropriate for a particular male animal.

Although the compounds of the invention are envisaged primarily for the treatment of erectile dysfunction or male sexual dysfunction, they are also useful for the treatment of female sexual dysfunction including orgasmic dysfunction related to clitoral disturbances, premature labour and dysmenorrhea.

The invention also provides a method of treating erectile dysfunction in a male animal which comprises administering an effective amount of a compound which is a selective cGMP-PDE inhibitor as defined above.

As stated above, one of the groups of compounds of selective cGMP PDE inhibitors are 4-aminoquinazoline derivative as disclosed in European patent application 0579496. This document claims a quinazoline derivative of the formula:

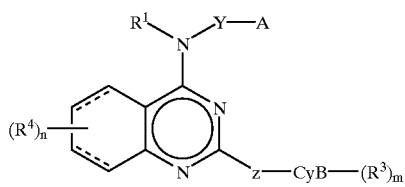

(I)

wherein—represents a single or double bond;
$R^1$ is hydrogen or $C_{1-4}$ alkyl;
Y is a single bond or $C_{1-6}$ alkylene;
A is
  (i) —CyA—$(R^2)_l$,
  (ii) —O—$R^0$ or —S(O)$_p$—$R^0$, or
  (iii) —NR$^{16}$R$^{17}$;
in which $R^0$ is hydrogen, $C_{1-4}$ alkyl, hydroxy $C_{1-4}$ alkyl or —CyA—$(R^2)_l$;
$R^{16}$ and $R^{17}$ independently are hydrogen or $C_{1-4}$ alkyl;
p is 0–2;
CyA is
  (1) a 3–7 membered, saturated or unsaturated carbocycle,
  (2) a 4–7 membered, unsaturated or partially saturated heterocycle containing one nitrogen atom,
  (3) a 4–7 membered, unsaturated or partially saturated heterocycle containing one nitrogen atom and one oxygen atom,
  (4) a 4–7 membered, unsaturated or partially saturated heterocycle containing one nitrogen atom and two oxygen atoms,
  (5) a 4–7 membered, unsaturated or partially saturated heterocycle containing two nitrogen atoms and one oxygen atom,
  (6) a 4–7 membered, unsaturated or partially saturated heterocycle containing one or two sulfur atoms,
  (7) a 4–7 membered, unsaturated, partially saturated or fully saturated heterocycle containing one or two oxygen atoms;
$R^2$ is (1) hydrogen, (2) $C_{1-4}$ alkyl, (3) $C_{1-4}$ alkoxy, (4) —COOR$^5$, in which $R^5$ is hydrogen or $C_{1-4}$ alkyl, (5) —NR$^6$R$^7$, in which $R^6$ and $R^7$ independently are hydrogen or $C_{1-4}$ alkyl, (6) —SO$_2$NR$^6$R$^7$, in which $R^6$ and $R^7$ are as hereinbefore defined, (7) halogen, (8) trifluoromethyl, (9) nitro or (10) trifluoromethoxy;
Z is a single bond, methylene, ethylene, vinylene or ethynylene;
CyB is
  (1) a 4–7 membered, unsaturated or partially saturated heterocycle containing one nitrogen atom,
  (2) a 4–7 membered, unsaturated or partially saturated heterocycle containing two nitrogen atoms,
  (3) a 4–7 membered, unsaturated or partially saturated heterocycle containing three nitrogen atoms,
  (4) a 4–7 membered, unsaturated or partially saturated heterocycle containing one or two oxygen atoms,
  (5) a 4–7 membered, unsaturated or partially saturated heterocycle containing one or two sulfur atoms,
$R^3$ is hydrogen, $C_{1-4}$ alkyl, $C_{1-4}$ alkoxy, halogen or trifluoromethyl;
$R^4$ is (1) hydrogen, (2) $C_{1-4}$ alkyl, (3) $C_{1-4}$ alkoxy, (4) —COOR$^8$, in which $R^8$ is hydrogen or $C_{1-14}$ alkyl, (5) —NR$^9$R$^{10}$, in which $R^9$ is hydrogen, $C_{1-4}$ alkyl or phenyl($C_{1-4}$ alkyl) and $R^{10}$ is hydrogen or $C_{1-4}$ alkyl, (6) —NHCOR$^{11}$, in which $R^{11}$ is $C_{1-4}$ alkyl, (7) —NHSO$_2$R$^{11}$, in which $R^{11}$ is as hereinbefore defined, (8) SO$_2$NR$^9$R$^{10}$ in which $R^9$ and $R^{10}$ are as hereinbefore defined, (9) —OCOR$^{11}$, in which $R^{11}$ is as hereinbefore defined, (10) halogen, (11) trifluoromethyl, (12) hydroxy, (13) nitro, (14) cyano, (15) —SO$_2$N=CHNR$^{12}$R$^{13}$ in which $R^{12}$ is hydrogen or $C_{1-4}$ alkyl and $R^{13}$ is $C_{1-4}$ alkyl, (16) —CONR$^{14}$R$^{15}$ in which $R^{14}$ is hydrogen or $C_{1-4}$ alkyl or phenyl($C_{1-4}$ alkyl) and $R^{15}$ is $C_{1-4}$ alkyl or (17) $C_{1-4}$ alkylthio, (18) $C_{1-4}$ alkylsulfinyl, (19) $C_{1-4}$ alkylsulfonyl, (20) ethynyl, (21) hydroxymethyl, (22) tri($C_{1-4}$ alkyl)silylethynyl or (23) acetyl;
and l, m and n independently are 1 or 2;
with the proviso that
  (1) CyA—$(R^2)_l$, does not represent cyclophentyl or trifluoromethylphenyl when Y is a single bond,
  (2) CyB does not bond to Z through a nitrogen atom when Z is vinylene or ethynylene,
  (3) CyB is not pyridine or thiophene when CyA is a 4–7 membered unsaturated, partially saturated or fully saturated heterocycle containing one or two oxygen atoms, and
  (4) Y is not a single bond when A is (ii) —O—$R^0$ or —S(O)$_p$—$R^0$ or (iii)—NR$^{16}$R$^{17}$; or a pharmaceutically acceptable salt thereof, or a hydrate thereof.

The reader is referred to the original patent document, EP 0 579 496 A1 for a complete discussion and disclosure of syntheses, representative compounds, and so forth, falling within its scope.

What is claimed is:

1. A method of treating erectile dysfunction in a male animal, comprising administering to an animal in need of said treatment an effective amount of a quinazoline derivative of the formula:

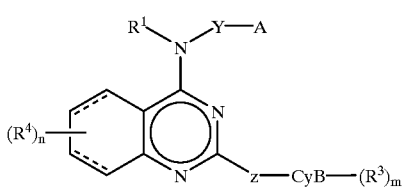

(I)

wherein—represents a single or double bond;
$R^1$ is hydrogen or $C_{1-4}$ alkyl;
Y is a single bond or $C_{1-6}$ alkylene;
A is
  (i) —CyA—$(R^2)_l$,
  (ii) —O—$R^0$ or —S(O)$_p$—$R^0$, or
  (iii) —NR$^{16}$R$^{17}$;
in which $R^0$ is hydrogen, $C_{1-4}$ alkyl, hydroxy $C_{1-4}$ alkyl or —CyA—$(R^2)_l$;

$R^{16}$ and $R^{17}$ independently are hydrogen or $C_{1-4}$ alkyl;

p is 0–2;

CyA is
(1) a 3–7 membered, saturated or unsaturated carbocycle,
(2) a 4–7 membered, unsaturated or partially saturated heterocycle containing one nitrogen atom,
(3) a 4–7 membered, unsaturated or partially saturated heterocycle containing one nitrogen atom and one oxygen atom,
(4) a 4–7 membered, unsaturated or partially saturated heterocycle containing one nitrogen atom and two oxygen atoms,
(5) a 4–7 membered, unsaturated or partially saturated heterocycle containing two nitrogen atoms and one oxygen atom,
(6) a 4–7 membered, unsaturated or partially saturated heterocycle containing one or two sulfur atoms,
(7) a 4–7 membered, unsaturated, partially saturated or fully saturated heterocycle containing one or two oxygen atoms;

$R^2$ is (1) hydrogen, (2) $C_{1-4}$ alkyl, (3) $C_{1-4}$ alkoxy, (4)—$COOR^5$, in which $R^5$ is hydrogen or $C_{1-4}$ alkyl, (5) —$NR^6R^7$, in which $R^6$ and $R^7$ independently are hydrogen or $C_{1-4}$ alkyl, (6) —$SO_2NR^6R^7$, in which $R^6$ and $R^7$ are as hereinbefore defined, (7) halogen, (8) trifluoromethyl, (9) nitro or (10) trifluoromethoxy;

Z is a single bond, methylene, ethylene, vinylene or ethynylene;

CyB is
(1) a 4–7 membered, unsaturated or partially saturated heterocycle containing one nitrogen atom,
(2) a 4–7 membered, unsaturated or partially saturated heterocycle containing two nitrogen atoms,
(3) a 4–7 membered, unsaturated or partially saturated heterocycle containing three nitrogen atoms,
(4) a 4–7 membered, unsaturated or partially saturated heterocycle containing one or two oxygen atoms,
(5) a 4–7 membered, unsaturated or partially saturated heterocycle containing one or two sulfur atoms, $R^3$ is hydrogen, $C_{1-4}$ alkyl, $C_{1-4}$ alkoxy, halogen or trifluoromethyl;

$R^4$ is (1) hydrogen, (2) $C_{1-4}$ alkyl, (3) $C_{1-4}$ alkoxy, (4)—$COOR^8$, in which $R^8$ is hydrogen or $C_{1-4}$ alkyl, (5) —$NR^9R^{10}$, in which $R^9$ is hydrogen, $C_{1-4}$ alkyl or phenyl($C_{14}$ alkyl) and $R^{10}$ is hydrogen or $C_{1-4}$ alkyl, (6)—$NHCOR^{11}$, in which $R^{11}$ is $C_{1-4}$ alkyl, (7) —$NHSO_2R^{11}$, in which $R^{11}$ is as hereinbefore defined, (8) $SO_2NR^9R^{10}$ in which $R^9$ and $R^{10}$ are as hereinbefore defined, (9) —$OCOR^{11}$, in which $R^{11}$ is as hereinbefore defined, (10) halogen, (11) trifluoromethyl, (12) hydroxy, (13) nitro, (14) cyano, (15) —$SO_2N=CHNR^{12}R^{13}$ in which $R^{12}$ is hydrogen or $C_{1-4}$ alkyl and $R^{13}$ is $C_{1-4}$ alkyl, (16) —$CONR^{14}R^{15}$ in which $R^{14}$ is hydrogen or $C_{1-4}$ alkyl or phenyl($C_{1-4}$ alkyl) and $R^{15}$ is $C_{1-4}$ alkyl or (17) $C_{1-4}$ alkylthio, (18) $C_{1-4}$ alkylsulfinyl, (19) $C_{1-4}$ alkylsulfonyl, (20) ethynyl, (21) hydroxymethyl, (22) tri($C_{1-4}$ alkyl)silylethynyl or (23) acetyl; and l, m and n independently are 1 or 2;

with the proviso that
(1) CyA—$(R^2)_l$ does not represent cyclopentyl or trifluoromethylphenyl when Y is a single bond,
(2) CyB does not bond to Z through a nitrogen atom when Z is vinylene or ethynylene,
(3) CyB is not pyridine or thiophene when CyA is a 4–7 membered unsaturated, partially saturated or fully saturated heterocycle containing one or two oxygen atoms, and
(4) Y is not a single bond when A is (ii) —O—$R^0$ or —S(O)$_p$—$R^0$ or (iii) —$NR^{16}R^{17}$;

or a pharmaceutically acceptable salt thereof, or a hydrate thereof.

2. A method as claimed in claim 1, wherein said compound is 4-phenylmethylamino-6-chloro-2-(1-imidazolyl)-quinazoline.

3. A method as claimed in claim 1, wherein said male animal is a male human.

* * * * *